United States Patent
Kaufhold

(10) Patent No.: US 6,423,189 B1
(45) Date of Patent: Jul. 23, 2002

(54) PROCESS FOR THE PREPARATION OF 1,3-DICHLOROPROPANE

(75) Inventor: Manfred Kaufhold, Marl (DE)

(73) Assignee: Degussa AG, Dusseldorf (DE)

( * ) Notice: Subject to any disclaimer, the term of this patent is extended or adjusted under 35 U.S.C. 154(b) by 0 days.

(21) Appl. No.: 09/580,562

(22) Filed: May 30, 2000

(30) Foreign Application Priority Data

Jun. 9, 1999 (DE) .......................................... 199 26 165

(51) Int. Cl.$^7$ .......................... B01D 3/00; C07C 17/361; C07C 19/01
(52) U.S. Cl. ............................. 203/14; 203/29; 203/38; 203/71; 570/259; 570/262
(58) Field of Search .............................. 203/34, 28, 29, 203/DIG. 6, 14, 71, 38; 570/259, 262

(56) References Cited

U.S. PATENT DOCUMENTS

| 2,084,710 | A | | 3/1937 | Spurlin | |
|---|---|---|---|---|---|
| 3,067,267 | A | | 12/1962 | Young et al. | ................ 570/259 |
| 3,644,546 | A | | 2/1972 | Hay et al. | ................... 570/259 |
| 3,998,706 | A | * | 12/1976 | Fruhwith et al. | ............... 203/7 |
| 5,364,987 | A | | 11/1994 | Haas et al. | ................. 570/259 |
| 5,552,037 | A | * | 9/1996 | Kalnes et al. | ................ 585/733 |

FOREIGN PATENT DOCUMENTS

| DE | 659 927 | 5/1938 |
|---|---|---|
| DE | 859 734 | 12/1952 |
| DE | 39 17 190 A1 | 11/1990 |
| DE | 39 17 190 | 11/1990 |
| DE | 196 06 549 | 8/1997 |
| WO | WO 97/44302 | 11/1997 |

OTHER PUBLICATIONS

Edwards, Eric D. (Castrol Ltd). "Halogenated Polyethers for addition to Lubricants or as Intermediates", Ref. #59: 12578–g–h, 1257a, 59:68404.*

E. Müller, Houden–weyl, Methoden Der Organischen Chemie, vol. 3, pp. 838–840, "Herstellung von Chlroverbindungen,"0 1962.

Phil. Hail. G. Higetag, Organisch–chemische Experimentierkunst, pp. 241–243, "Herstellung der Kohlenstoff–Halogenbindungen" 1970.

F. Richter, Beilsteins Handbuch der Organischen Chemie, vol. 1, p. 227, "1.3 Dichlor–Propan," 1958.

Jerzy Myszkowski, et al., Chemical Abstracts, vol. 110, No. 7, p. 635, Feb. 13, 1989, AN 110:57108k, "Process for Manufacturing 1,3–Dichloropropane", Dec. 31, 1988.

Z.F. Mullakhmetova, Chemical Abstracts, vol. 109, No. 9, p. 647, AN 109:72980m, Aug. 29, 1988, "Reactions of 1,3–Dioxacycloalkanes with Halosilanes", 1987.

* cited by examiner

Primary Examiner—Virginia Manoharan
(74) Attorney, Agent, or Firm—Oblon, Spivak, McClelland, Maier & Neustadt, P.C.

(57) ABSTRACT

A process for the preparation of 1,3-dichloropropane by reacting bis(3-hydroxypropyl)ether with hydrogen chloride, optionally in the presence of tertiary basic nitrogen compounds or other tertiary aliphatic bases as catalysts, distilling off the 1,3-dichloropropane and the water of reaction and working up the two phases.

6 Claims, No Drawings

PROCESS FOR THE PREPARATION OF 1,3-DICHLOROPROPANE

BACKGROUND OF THE INVENTION

1. Field of the Invention

The invention relates to a process for the preparation of 1,3-dichloropropane by reacting bis(3-hydroxypropyl)ether with hydrogen chloride, preferably in the presence of a tertiary basic nitrogen compound or other tertiary aliphatic base as a catalyst, distilling off the 1,3-dichloropropane and the water of reaction, and working up the two phases.

2. Background of the Invention 1,3-Dichloropropane is an important intermediate for the preparation of pharmaceuticals and agrochemicals and also serves as a low-toxic solvent. Syntheses of 1,3-dichloropropane have been known for a long time from the literature. Most start from 1,3-propanediol, reacting with thionyl chloride or phosphorus pentachloride (see Clark Streight, Trans. roy. Soc. Canada (3) 23, 3, (1929) 77).

A disadvantage of this process is the relatively high cost of the starting material 1,3-propanediol. There is, however, a great interest in a process which proceeds economically with a low-cost starting material and which is as easy to realize industrially as the customary processes for the preparation of chlorine compounds from the corresponding hydroxyl compounds.

The object of the invention was therefore to find a suitable starting material for the synthesis of 1,3-dichloropropane which is low-cost and available in a sufficient amount.

SUMMARY OF THE INVENTION

The object is achieved according to the invention by using bis(3-hydroxypropyl)ether as starting material. This etherdiol is produced as a byproduct in the production of 1,3-propanediol and which, according to EP-A-0 577 972, can only be cleaved by a specific complex process step.

Surprisingly, it has now, however, been found that under conditions under which the hydroxyl groups of the etherdiol are exchanged for chlorine atoms, the ether group is also cleaved and that 1 mol of etherdiol and 4 mol of hydrogen chloride give 2 mol of 1,3-dichloropropane and 3 mol of water according to the equation

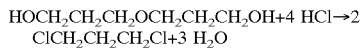

$$HOCH_2CH_2CH_2OCH_2CH_2CH_2OH + 4\ HCl \rightarrow 2\ ClCH_2CH_2CH_2Cl + 3\ H_2O$$

The invention thus provides a process for the preparation of 1,3-dichloropropane, which comprises reacting bis(3-hydroxypropyl)ether, preferably in the presence of tertiary basic nitrogen compounds or other tertiary aliphatic base, with hydrogen chloride, distilling off the 1,3-dichloropropane and water of reaction which form and working up the two phases together.

DETAILED DESCRIPTION OF THE PREFERRED EMBODIMENTS

3-Chloropropanol forms as an intermediate. Bis(3-chloropropyl)ether forms in a small amount depending on the distillation conditions during the reaction. It can be returned to the reaction. The ready cleavability of the ether using hydrogen chloride is contrary to information in the literature: for example, "Houben-Weyl" (Halogen compounds volume, Georg Thieme Verlag Stuttgart, 1962, pages 839 and 840) states that cyclic ethers, such as, for example, tetrahydrofuran and allyl ethers can be cleaved relatively easily, (but) that the saturated aliphatic ethers can only be converted into the chlorides using hydrogen chloride under extreme conditions. In addition, the monograph "Organisch-Chemische Experimentierkunst" by Weygand/Hilgetag (Johann Ambrosius Barth Verlag Leipzig, 1970) states, on page 241, in connection with ether cleavage using hydrogen halides: "Of the hydrogen halides, HI is particularly effective, HBr less so, HCl least so". According to this, it was thus to be assumed that the etherdiol is only just cleaved with hydrogen chloride.

The process according to the invention does not usually require a solvent. If, for whatever reason, however, it should be advantageous, possible solvents are, for example, aliphatic or aromatic hydrocarbons, halogen compounds and aliphatic ethers.

Tertiary basic nitrogen compounds acting as catalysts are advantageously used in an amount such that they adopt the function of a solvent.

Suitable tertiary basic nitrogen compounds are pyridine and alkylpyridines such as methyl-, dimethyl- and ethylpyridine, and technical-grade mixtures of these compounds (so-called pyridine bases), and also quinoline and derivatives of quinoline, such as, for example, 2-methylquinoline (quinaldine) and 4-methylquinoline (lepidine), N,N-dialkylaniline, such as N,N-dimethylaniline, and tertiary amines, such as trialkylamines and mixtures of the above compounds. Preference is given to using so-called pyridine bases. These are in the form of hydrochlorides during and after the reaction and, in this form, can be separated off easily and be used repeatedly one after the other.

In the continuous procedure, etherdiol and hydrogen chloride are added simultaneously to the reactor to the pyridine bases present as hydrochlorides, and 1,3-dichloropropane and water are distilled off.

In the presence of tertiary basic nitrogen compounds, explained using pyridine bases as an example, the procedure can be as follows:

A pyridine base mixture is introduced initially and hydrogen chloride is introduced to saturation. The etherdiol is then added, and the mixture is heated from about 20° C. to about 120° C. while passing in hydrogen chloride. The ratio of pyridine base to etherdiol is from 0.1 mol to 5 mol, preferably from 0.5 mol to 1.5 mol to 2 mol. The amount of hydrogen chloride depends on its rate of absorption. It is introduced at a rate such that there is always a slight excess in the reactor. In order that the reaction proceeds quickly enough, the temperature is increased to about 190° C., preferably to 160° C. over the course of time. During the reaction, a mixture of 1,3-dichloropropane and water is continuously distilled off. This mixture is worked up in a manner known per se, and the dichloropropane is purified by distillation.

The only partially reacted products 3-chloropropanol and bis(3-chloropropyl)ether can be returned to the reaction.

The example below serves to illustrate the process according to the invention in more detail, but does not intend to limit it to the circumstances specifically given.

EXAMPLE

The reaction apparatus was made from glass and consisted of a four-necked flask fitted with stirrer, thermometer, dropping funnel, gas inlet pipe and an attached distillation bridge with receiver.

The flask was charged with 93.1 g of pyridine base (technical-grade mixture of pyridine, methylpyridine and ethylpyridine) and 18.6 g of water.

Gaseous hydrogen chloride was introduced into this mixture to saturation with cooling at room temperature. Water was added to keep the solution liquid. 268.4 g (2 mol) of bis(3-hydroxypropyl)ether were then added at room temperature, and more hydrogen chloride was introduced. With the introduction of further hydrogen chloride, the mixture was then heated to 120° C. in 0.5 hours. At this temperature the hydrogen chloride was quickly absorbed, and the reaction products and water began to distill off. After about 4 hours, the absorption of hydrogen chloride subsided. The temperature was increased to 160° C. over the course of 4 hours. After a total of 19 hours, the reaction was complete.

114 g of cyclohexane were added to the distillate and water was thus removed azeotropically. The residue was then worked up by distillation. The main fraction obtained was 1,3-dichloropropane. The bottom product consisted of 3-chloropropan-1-ol and bis(3-chloropropyl)ether. The two products were returned to the reaction and produced, like the feed diol (in the next batch), further 1,3-dichloropropane. In calculating the yield, which relates to the conversion, these molar amounts were therefore taken into consideration.

In the main fraction 280.3 g of 1,3-dichloropropane with a purity of 99.1% were obtained. The yield based on the feed was 61.4%. The distillation produced 24.0 g of 3-chloropropan-1-ol (calculated as 100% pure) and 65.3 g of bis(3-chloropropyl)ether (calculated as 100% pure) which, because of their reuse, were regarded as unreacted feed product when calculating the yield. From this, the yield of 1,3-dichloropropane based on (complete) conversion was calculated as about 85%.

This application is based on German patent application DE 19926165.2-42 filed in the German Patent Office on Jun. 9, 1999, the entire contents of which are hereby incorporated by reference.

What is claimed is:

1. A process for the preparation of 1,3-dichloropropane, which comprises reacting bis(3-hydroxypropyl)ether with hydrogen chloride; and distilling off 1,3-dichloropropane and water from said reaction providing two phases and working up the two phases.

2. The process as claimed in claim 1, wherein said reaction is carried out in the presence of a tertiary basic nitrogen compound.

3. The process as claimed in claim 1, wherein said reaction is carried out in the presence of a compound selected from the group consisting of pyridine, alkylpyridine, quinoline, quinoline derivatives, N,N-dialkylalinine trialkylamines and mixtures of pyridine and alkylpyridine.

4. The process as claimed in claim 1, wherein said reaction takes place at a temperature between 20° C. and 190° C.

5. A process for the preparation of 1,3-dichloropropane, which comprises reacting bis(3-hydroxypropyl)ether with hydrogen chloride; and distilling off 1,3-dichloropropane and water from said reaction providing two phases and working up the two phases, wherein during said reaction, a mixture of reaction products and water is continuously distilled off, water is azeotropically removed from a distillate and a residue is worked up by distillation.

6. A process as claimed in claim 1, wherein partially reacted products 3-chloropropanol and bis(3-chloropropyl)ether are returned to the reaction.

* * * * *